United States Patent [19]

Bohler et al.

[11] Patent Number: 4,457,623

[45] Date of Patent: Jul. 3, 1984

[54] ATOMIC ABSORPTION SPECTROPHOTOMETER PROVIDING BACKGROUND CORRECTION USING THE ZEEMAN EFFECT

[75] Inventors: Walter Bohler, Wilton; Thomas W. Barnad, Weston, both of Conn.

[73] Assignee: The Perkin-Elmer Corporation, Norwalk, Conn.

[21] Appl. No.: 237,199

[22] Filed: Feb. 23, 1981

[51] Int. Cl.³ .................................................. G01J 3/42
[52] U.S. Cl. .................................................... 356/307
[58] Field of Search ............... 356/307, 312, 315, 311; 350/402

[56] References Cited

U.S. PATENT DOCUMENTS 4,341,470  7/1982  Parker et al. ..................... 350/307

OTHER PUBLICATIONS

Steinmetz et al., *Applied Optics*, vol. 6, No. 6, Jun. 1967, pp. 1001–1004.
Rahn et al., *Applied Spectroscopy*, vol. 25, No. 6, 1971, pp. 675–677.
Kahn et al., Conference: 17th *International Spectroscopy Colloquium*, vol. 1, Florence, Italy, Sep. 1973, pp. 16–22.

*Primary Examiner*—F. L. Evans
*Attorney, Agent, or Firm*—F. L. Masselle; E. T. Grimes; R. A. Hays

[57] ABSTRACT

An atomic absorption spectrophotometer having a source, e.g., a hollow cathode lamp, of spectral radiation of a selected narrow band of wavelengths optically directed along an axis through an electrothermic sample atomizer and a field stop to a photoelectric detector. The sample atomizer is subjected to a substantially unipolar AC electromagnetic field having flux lines directed transversely to said axis to effect Zeeman splitting of the radiation into two orthogonally polarized components π and σ. Disposed in the optical path between the atomizer and detector is a stationary beam-splitting polarizer prism oriented so as to transmit the σ polarized component and block the π component. Mirrors are used exclusively in the optical systems so as to minimize the effect of dispersion and stray light.

An electromagnet, used to generate the electromagnetic field, is connected to the AC power line in series with the diode and has a small capacitor connected across its coils. This causes the magnetic field at the sample atomizer to vary sinusoidally from a maximum value of one polarity to a very small value of the opposite polarity. The polarizer prism is of unique design in which one polarization passes through undeviated on the optical axis while the other is diverted to one side on the other. The ray passing through the prism along the optical axis is uniquely depolarized upon exiting. A field stop is located between the prism and the atomizer and restricts the field of view of the prism to an angle less than or equal to its restricted field of view, excludes blackbody radiation of the furnace, and limits the aperture at the source.

31 Claims, 9 Drawing Figures

ATOMIC ABSORPTION SPECTROPHOTOMETER PROVIDING BACKGROUND CORRECTION USING THE ZEEMAN EFFECT

TECHNICAL FIELD

This invention relates to apparatus for utilizing the Zeeman (or Stark) effect for achieving background correction in atomic absorption spectrophotometers (AAS); more particularly, it relates to a unique combination of features which provides several times greater insensitivity to background absorption than heretofore attained in the prior art and enables the correction system to take the form of an accessory applicable to existing atomic absorption spectrophotometers.

BACKGROUND ART

Atomic absorption spectrophotometry is utilized to measure the concentration of a particular element in a sample. For example: if one wishes to determine the concentration of copper in a sample, a light source producing one of the characteristic spectral lines of copper is utilized in the spectrophotometer. These are most often hollow cathode or electrodeless discharge lamps where the cathode is of copper, or any other element to be measured. A monochromator usually utilizing a diffraction grating disperses the light from the hollow cathode into a spectrum and the monochromator is adjusted so that the line of interest falls upons a detector, usually a photomultiplier tube. The amount of light falling on the photo tube is measured as a reference.

A sample of material in which one wishes to determine the amount of copper is then introduced into the path of the light from the line source to the monochromator. The sample must be "disassociated" so that the copper atoms are free and not a part of a molecular compound in which case they would not provide their characteristic spectrum. This may be accomplished in an absorption furnace (electrothermic sample atomizer). When the copper atoms are introduced into the light path they absorb light at the same characteristic spectral lines at which the copper atoms in the light source emit light. Thus, at the line of interest, light will be absorbed and less light will fall on the photomultiplier tube. The natural logarithm of the signal from the photo tube when there is no absorbance divided by the signal when the copper is present in the light path to absorb the light is called the absorbance, and from the absorbance the concentration of copper in the sample may be determined.

There is one basic problem in all atomic absorption spectrophotometry. This is the so-called background absorbance, sometimes termed "non-atomic absorption" or "molecular absorption". The problem is that other atoms and molecules in the sample may also absorb light at the characteristic spectral line of interest. This absorption will of course cause an error in the absorbance measured. Various means have been disclosed in the prior art to correct the problem and in general such systems are called "background correction".

The most common form of background correction utilized in commercial atomic absorption spectrophotometers is the continuum source system. In this system light from a broad band light source, that is, one producing a continuous, rather than a line spectrum, is utilized to measure the absorbance of a sample. Another beam is passed through the sample from a characteristic line source. The absorbance is then measured at the line of interest and it is assumed that if one subtracts the absorbance from the continuous line source one will derive the absorbance at the spectral line of interest. There are many problems with such systems. The light from the characteristic line source and the light from the continuous source do not pass through the same path and there may be substantial differences in the concentrations of the sample in the two paths, leading to systematic error.

If a sequential beam system is utilized, wherein the continuous spectrum reference beam is first passed through the sample and thereafter the line source beam, the concentration may vary over time as well as space, again introducing systematic errors.

Another method of background correction has been proposed. This utilizes the Zeeman or Stark effects. In the Zeeman or Stark effects, when a magnetic or an electric field is applied to the sample, the spectral lines characteristic of an atom are split into several spectral lines.

In the normal Zeeman and Stark effects of interest here, a spectral line may be converted into two spectral lines shifted to either side of the normal spectral line, by an amount proportional to the applied field, or into three spectral lines, one at the normal position and two shifted, as aforesaid.

An important feature of the Stark and Zeeman effects is that the split spectral lines do not all have the same polarization and in particular the polarization of the central or normal central line and the shifted spectral lines will be different, thus making it possible to look at the normal line or the shifted lines with a polarization analyzer.

Below are listed a number of prior art patents and publications describing various systems utilizing the Stark or Zeeman effects for background correction in atomic absorption spectrophotometry.

| Pat. No. | Inventor | Date |
| --- | --- | --- |
| | U.S. PAT. NOS. | |
| 3,676,004 | Prugger et al | 7/11/72 |
| 3,811,778 | Hadeishi | 5/21/74 |
| 3,914,054 | Hadeishi | 10/21/75 |
| 3,937,577 | Dorsch | 2/10/76 |
| 4,035,083 | Woodriff et al | 7/12/77 |
| 4,171,912 | Ito et al | 10/23/79 |
| | U.K. PATENTS | |
| 918,878 | Isaak | 2/20/63 |
| 918,879 | Isaak | 2/20/63 |
| 1,271,170 | Zeiss-Stiftung | 4/19/72 |
| 1,385,791 | Parker and Pearl | 2/26/75 |
| 1,420,044 | US ERDA | 1/7/76 |

ARTICLES

Science, "Hyperfine Zeeman Effect Atomic Absorption Spectrometer for Mercury", Hadeishi, T. and McLaughlin, R. D.; Vol. 174, Oct. 22, 1971, pp. 404–407.

Analytical Chemistry, "New Zeeman Method for Atomic Absorption Spectrophotometry", Koizumi, H. and Yasuda, K.; Vol. 47, No. 9, Aug. 1975, pp. 1679–1682.

Talanta, "An Application of the Zeeman Effect to Analytical Atomic Spectroscopy-II", Stephens, R. and Ryan, D. E.; Vol. 22, pp. 659-662; Pergamon Press, 1975; printed in Great Britain.

Talanta, "An Application of the Zeeman Effect to Analytical Atomic Spectroscopy-I", Stephens, R. and Ryan, D. E.; Vol. 22, pp. 655-658; Pergamon Press, 1975; Printed in Great Britain.

The prior art may be catagorized as providing systems having a number of possible characteristics. The magnetic or electric field may be applied at the line source or at the absorption chamber. The field may be DC, that is on or off; it may be AC, for example sinusoidally varying; it may be unipolar, or bipolar, that is never going negative, or alternately going negative and positive; the polarization analyzer may be located before or after the absorption chamber; it may be static or rotating; and the optical axis of the system through which the light passes may be parallel to or transverse to the applied field. Clearly, there is a vast number of combinations of possible elements to provide systems utilizing the Zeeman or the Stark effect for background correction.

However, we have found that all of the prior art systems do not utilize or suggest what we have discovered to be the ideal combinations of elements for such systems.

For example, in the early British Pat. Nos. 918,878, and 918,879, a double beam system is proposed subject to all of the aforesaid problems of double beam systems. British Pat. No. 1,385,791 describes a multiplicity of possible systems, but does not indicate any advantage or disadvantage, depending on whether the field is applied at the absorption chamber or at the line source (except for lamp non-linearities which have lately been overcome as described below); or where the polarization analyzer is placed in the system. U.S. Pat. No. 4,035,083 discloses an AC full wave magnetic system and a rotating polarizer system. No practical differences between the systems are discussed. U.S. Pat. No. 3,676,004 and corresponding British Pat. No. 1,271,170 discloses systems in which a magnetic field is applied at the line source and a rotating polarization analyzer is employed. U.S. Pat. No. 3,914,054 and corresponding British Pat. No. 1,420,044, U.S. Pat. Nos. 3,937,577, 3,811,778 and the articles by Hadeishi and McLaughlin, Stephens and Ryan, and Koizumi and Yasuda, all disclose fixed fields. Many of these systems have rotating analyzers. All of these systems apply the field at the line source.

U.S. Pat. No. 4,171,912 is concerned with double peak detection; utilizes polarizers both before and after the absorption cell; and applies the field at the sample. The article by Stephens and Ryan describes a DC discharge lamp which will maintain a stable plasma in a magnetic field and thus overcome the previously expressed objections to applying the field to the light source.

U.S. Pat. Nos. 3,413,382, 3,544,789 and 3,689,158 disclose conventional non-Zeeman or Stark background correction.

If one applies the field to the line source rather than the absorption chamber one has all of the disadvantages previously described in continuum source systems. That is, what one does, utilizing the field at the line source, is to pass alternately through the absorption chamber the line of interest, thus providing a measure of the absorption plus the background, and then the shifted Zeeman lines or line, to obtain the background absorption. Perturbing the light source causes the same types of errors as the sequential continuum source systems previously described. It is not believed that this disadvantage of applying the field to the line source has been recognized in the prior art.

If one uses a DC field, which is turned on and off to provide synchronous detection, or a field which is bipolar, energy must be stored alternately as the field collapses and restored to the field as the field is established, leading to the utilization of large capacitors or inductors, which add to the bulkiness and cost of the unit. Furthermore, if a magnetic field is used, the alternate magnetization of the poles and core of the magnet requires increased energy due to hysteresis.

The polarization analyzers normally used in Zeeman systems have disadvantages and rotating polarizers have severe disadvantages. In the Zeeman system it is normally desirable to operate at least part of the time in the ultraviolet portion of the spectrum. The birefringent polarization analyzers for this portion of the spectrum have restricted fields of view; that is, they only operate when light reaches them very small angles off the optical axis; they tend to have some non-uniformities in their crystalline structure which, when they are rotated, changes the amount of light passing through them regardless of the polarization, providing a false signal. The diffraction gratings used in the monochromators are not uniformly sensitive to light of different polarizations, having a preferred polarization or blazed direction, and therefore rotating any polarizer and then looking at it with the diffraction grating in the monochromator leads to a false signal.

Furthermore, prior art rotating polarizers exhibit non-uniform light transmission across their apertures. We have therefore found that the polarization analyzer in a Zeeman atomic absorption system should be static in order to obtain real improvement in background correction accuracy relative to continuum source systems.

There appears to be no discussion in the prior art as to where the aperture stop or the field stop of a Zeeman atomic absorption spectrophotometer should be located. We have found that there are certain ideal positions for these elements of the system which lead to maximum utilization of the light available, rejection of black body radiation from the furnace of the absorption cell, maximum utilization of the field of view of the polarizer, and independence of the size of the light source.

We have further discovered that if the high voltage power supply to the photomultiplier detector is controlled by an automatic gain control circuit responsive to the background signal in order, in the first instance, to increase the dynamic range of the instrument, that the high voltage signal applied to the photomultiplier is in fact proportional to the background absorption signal, derived with no computation whatsoever.

We have also found that a Zeeman atomic absorption system may be conveniently provided as an adapter for existing atomic absorption spectrophotometers, such as the Perkin-Elmer 5000.

OBJECTS OF THE INVENTION

It is therefore an object of the invention to provide an atomic absorption spectrophotometer exhibiting improved background correction.

It is another object of the invention to provide an adapter for converting an existing atomic absorption spectrophotometer into an atomic absorption spectrophotometer of the above character employing the Zeeman or Stark effect for background correction.

Another object of the invention is to provide an atomic absorption spectrophotometer of the above character employing the Zeeman or Stark effect for background correction in which the background signal and the absorption plus background signals are measured over the same optical path and at the same spectral line.

A further object of the invention is to provide a spectrophotometer of the above character employing very simple field generating means.

Still another object of the invention is to provide a spectrophotometer of the above character utilizing no moving parts.

A still further object of the invention is to provide a spectrophotometer of the above character employing synchronous detection.

Yet another object of the invention is to provide a spectrophotometer of the above character providing a simply derived background absorbance measurement.

Still yet another object of the invention is to provide a spectrophotometer of the above character wherein the background signal from the photo detector is kept constant.

A yet further object of the invention is to provide a spectrophotometer of the above character employing substantially no energy storage devices and substantially unipolar fields.

Another object of the invention is to provide a spectrophotometer of the above character insensitive to polarization effects in the monochromator.

A further object of the invention is to provide a spectrophotometer of the above character which rejects black body radiation from the absorption furnace thereof.

Yet still another object of the invention is to provide a spectrophotometer of the above character utilizing a polarization analyzer having a restricted field of view.

Yet still a further object of the invention is to provide a spectrophotometer of the above character employing a novel form of polarization analyzer which depolarizes the light exiting therefrom.

Still another object of the invention is to provide a spectrophotometer of the above character that makes maximum use of the light throughout.

Yet another object of the invention is to provide a spectrophotometer of the above character which operates without regard to the size of the light source employed.

Still a further object of the invention is to provide a spectrophotometer of the above character in which stray light effects are minimized.

Yet still another object of the invention is to provide a spectrophotometer of the above character employing the Zeeman effect for background correction.

Another object of the invention is to provide a novel polarization analyzer the output of which is depolarized.

A further object of the invention is to eliminate deleterious polarization effects in spectrometers employing polarization analyzers.

Other important objects of the invention are to provide a spectrophotometer of the above character providing increased sensitivity and accuracy, ease of operation, low manufacturing and operating costs, and which my utilize existing microcomputer architecture and programs.

Other objects of the invention will in part be obvious and will in part appear hereinafter.

The invention accordingly comprises features of construction, particular elements, arrangements of parts and a system which will be exemplified in the elements, constructions, and system hereinafter set forth. The scope of the invention will be indicated in the claims.

THE DRAWINGS

For a fuller understanding of the nature and objects of the invention, reference should be had to the following detailed description, taken in connection with the accompanying drawings, in which.

The same reference characters refer to the same elements throughout the several views of the drawings.

DISCLOSURE OF THE INVENTION

The system of the invention for background correction employs a field at the absorption furnace so that all absorbance measurements, with and without the sample signal, are made at the same spectral line. The field is substantially unipolar. For convenience a magnetic field is utilized and the electromagnet is connected directly to the alternating current power lines through a diode to provide the unipolar field. When the field is ON the background absorbance is measured. When the field is OFF the absorbance measured is the sum of the absorbance due to the sample and the background. Thus the absorbance of the sample may be measured by simple subtraction.

In order that the absorbance at substantially zero field may be measured over a significant length of time, the field is made to go slightly negative, so that over the measurement period the integral of the field is substantially zero. This is accomplished by connecting a small capacitor across the coil of the electromagnet.

The output of the photomultiplier when the field is ON is integrated and supplied to an automatic gain control circuit which controls the high voltage power supply to the photomultiplier. The result is that the high voltage potential supply to the photomultiplier is proportional to the log of the background signal and directly proportional to the background "absorbance" and this signal may be derived through a voltage divider and utilized directly by the operator.

A birefringent polarizer is employed so that the instrument may be operated in the ultraviolet. Materials that may be used include quartz, magnesium fluoride and sapphire. Artificial crystal quartz is the preferred material. The polarizer is used in a unique orientation which causes the undeviated ray along the optical axis to be depolarized as it exits from the polarizer, thus freeing the monochromator from polarization effects.

The polarizer is of the type which deviates the extraordinary rays from the optical axis and therefore the polarizer has a rather restricted field of view. The polarizer has exit and entrance faces which are perpendicular to the optical axis.

The polarizer is located between the absorption furnace and the monochromator so that light from the furnace will not be reflected off the exit surface of the polarizer, as would be the case if it were located before the furnace. Such stray light would pass through the absorption furnace twice and thus adversely affect the accuracy of the absorption measurement.

A field stop is employed between the absorption furnace and the polarization analyzer which restricts light reaching the analyzer to the analyzer's effective field of view. The field stop and polarization analyzer are located between the furnace and the monochromator such that the black body radiation from the walls of the absorption furnace are excluded from the field seen by the monochromator. Furthermore, the line source is located in the optical system such that the field stop restricts the field of view of the polarization analyzer to the active light source; that is the glowing hollow cathode in a hollow cathode lamp for example.

The entrance face of the polarization analyzer acts as the aperture stop of the system and the optical system is arranged such that this entrance face (in the direction of the slit) is imaged on and co-extensive with the diffraction grating of the monochromator for maximum light utilization efficiency.

Those skilled in the art will understand that many of the features of the invention could be accomplished in a Stark background correction instrument as well as in the Zeeman background correction instrument disclosed if a sufficiently large electric field were produced at the furnace.

We therefore use the expression "electromagnetic optical effect" in order to cover both the Stark and the Zeeman effects; that is both electric field effects and magnetic field effects. We also use the expression "electromagnetic field" to mean both the electric field used in the Stark effect and the magnetic field used in the Zeeman effect.

Reflecting optics, i.e. mirrors, are employed throughout the system, rather than lenses, in order to minimize the effects of dispersion and stray light.

BEST MODE FOR CARRYING OUT THE INVENTION

Figure 1:
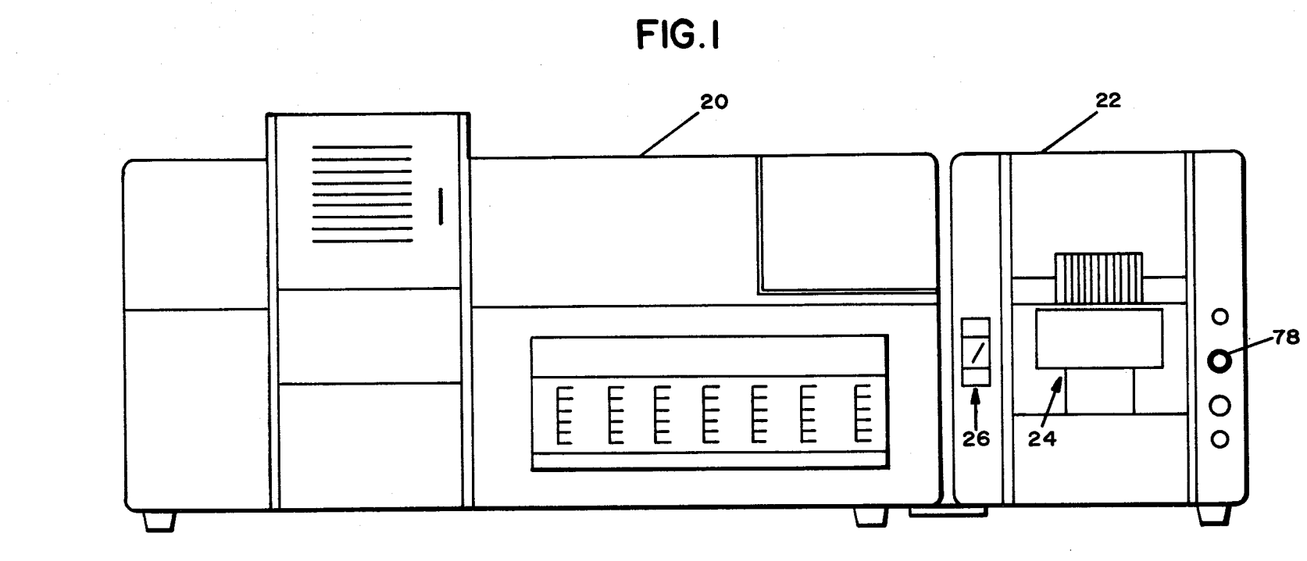
FIG. 1 is a front view of an adapter according to the invention for providing Zeeman background correction applied to a Perkin-Elmer Model 5000 atomic absorption spectrophotometer.

Now referring to FIG. 1, instrument 20 is a Perkin-Elmer Model 5000 atomic absorption spectrophotometer. A Zeeman background correction adapter 22 according to the invention is located to the right of the spectrophotometer 20. The magnet and absorption furnace are generally indicated at 24. A three-position switch generally indicated at 26, turns the magnet ON or OFF or allows it to be controlled remotely from the spectrophotometer 20.

Figure 2:
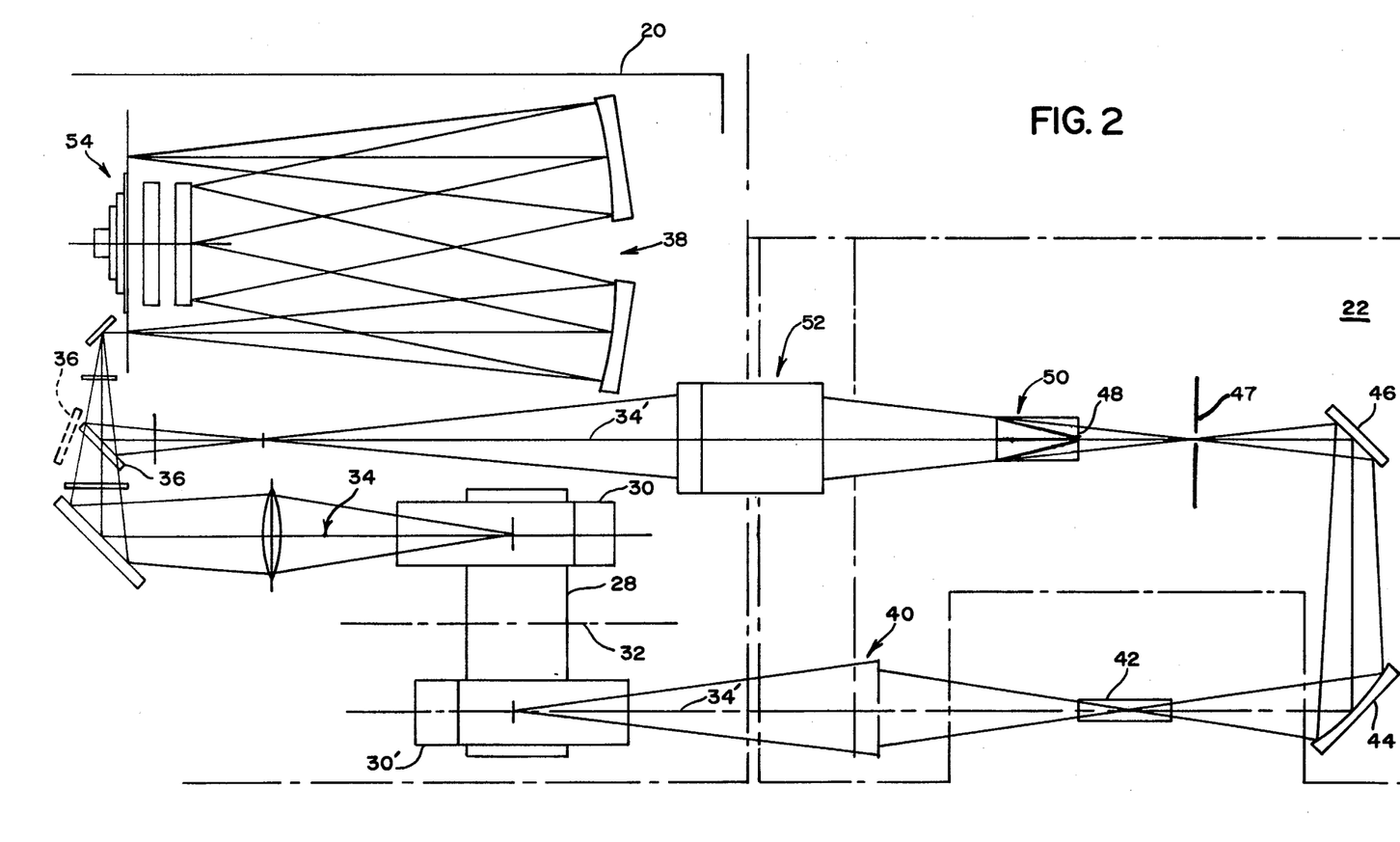
FIG. 2 is a diagramatic top view of the optical system of the adapter of the invention and of the Model 5000 spectrophotometer of FIG. 1.

Now referring to FIG. 2, the spectrophotometer 20 is provided with a carousel 28 in which a plurality of hollow cathode line sources 30 may be mounted. The carousel is rotatable about the axis 32 to bring the desired line source into alignment with the optical axis generally indicated at 34. Normally a two-positioned mirror 36 is located in its dotted position and light from the line source 30 proceeds to the monochromator and photomultiplier section of the instrument generally indicated at 38. The two-positioned mirror 36 is a new element added to the system so that it may be utilized with the adapter 22.

When the mirror 36 is at the solid line position the optical axis is diverted as shown at 34' to accept light from the adapter 22 into the monochromator photomultiplier section 38.

In order to supply light from a line source to the adapter 22, one or more of the hollow cathode lamps 30' are reversed in the carousel 28 so that their light proceeds out of the spectrophotometer 20 and into the adapter along optical axis 34'. The optical axis is stepped downwardly by mirror optics generally indicated at 40, so that the light is focused on the absorption furnace 42 (which may be a heated graphite analyzer) located between the poles of the magnet 24. The light exiting in the absorption furnace 42 is then diverted by mirrors 44 and 46 and supplied to the entrance face 48 of the polarization analyzer 50. The polarization analyzer 50 is oriented such that the $\pi$ polarization of the normal absorption line is blocked and the $\sigma$ polarization of the shifted absorption lines are undeviated and proceed along the optical axis 34' through another set of stepped optics generally indicated at 52 to bring the optical axis 34' into alignment with flip mirror 36 and thence to the monochromator and photomultiplier section generally indicated at 38. However, the line source 30' provides substantially no light at the displaced lines with the result that the absorption of the normal line in the $\sigma$ polarization state is due to background alone. The chopper generally indicated at 54 of the spectrophotometer 20 is not used when the Zeeman adapter 22 is in use.

Figure 3:
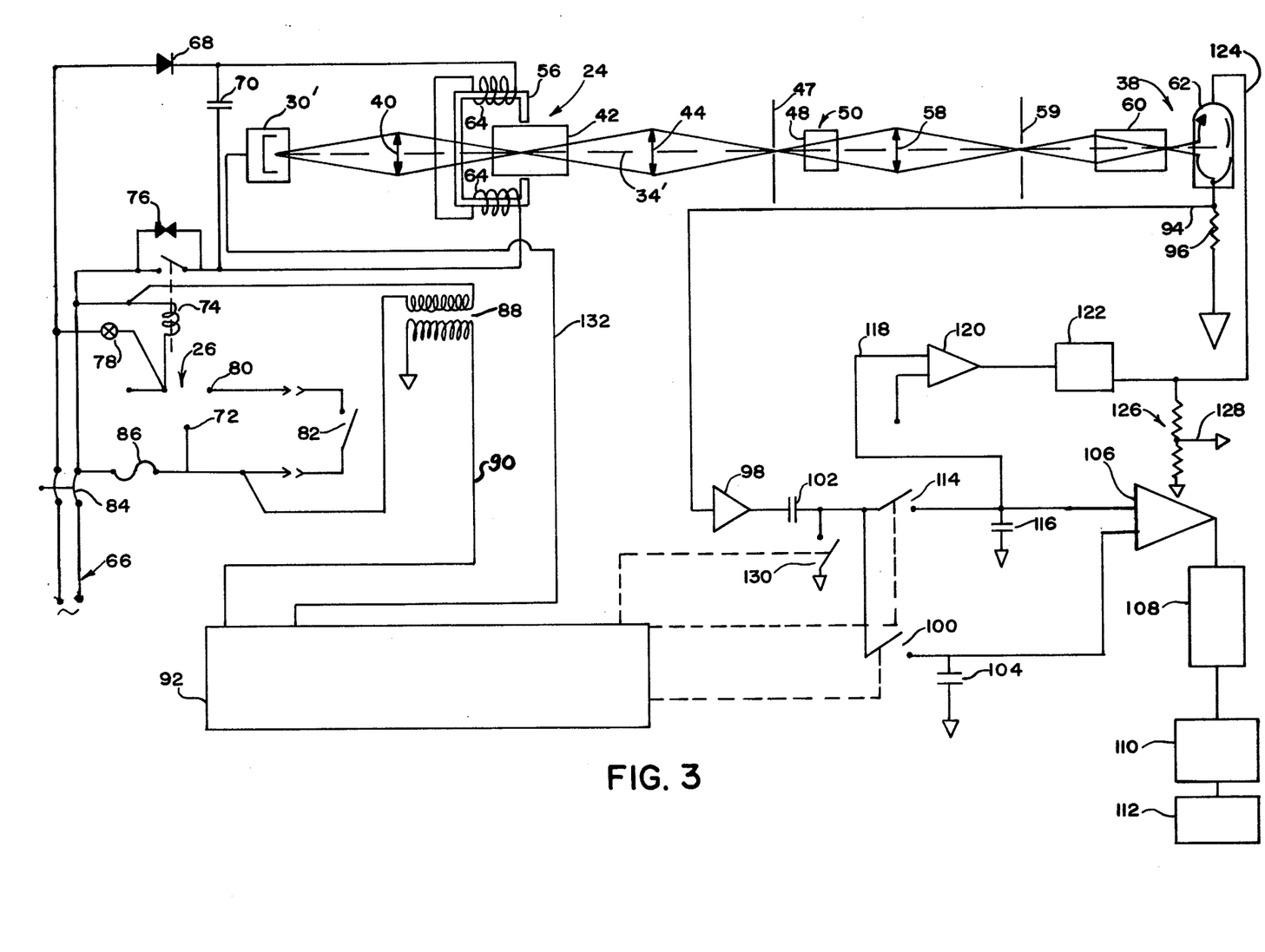
FIG. 3 is a schematic diagram of the system of the invention employing Zeeman background correction.

Now referring to FIG. 3. In schematic terms light from the line source 30' is focused by mirror optics 40 to within the absorption furnace 42 located between the poles of an electromagnet 56. The optic axis 34' is perpendicular to the field. Light is then refocused by mirror optics 44 on an aperture stop 47. Light from the aperture stop 47 passes through a polarization analyzer 50 is then refocused by mirror optics generally indicated at 58 on the slit 59 of a monochromator 60 which thence focuses light around the spectral line of interest upon a photomultiplier 62.

The coils 64 of the electromagnet 56 are connected across an ordinary AC power line generally indicated at 66. The coils 64 are energized through a series connected diode 68. This causes the current to the coils, and thus the magnetic field between the poles, to be essentially unipolar. In order that the field not be merely instantaneously zero but substantially zero for a longer length of time a small two microfarad capacitor 70 is connected across the coils 64.

Multi-position switch 26 is shown in its off position. When connected to pole 72, relay 74 is energized closing the circuit to the electromagnet 56. Surge protection is provided by surge protector 76. Simultaneously, lamp 78, which may be conveniently located on the front panel (FIG. 1), energizes.

When switch 26 is connected to pole 80 the electromagnet may be turned ON by a remote switch 82 located within the spectrophotometer 20. Circuit protection is provided by circuit breaker 84 and fuse 86.

The primary coil of a signal transformer 88 is connected in series with the relay 74. One side of the secondary of transformer 88 is connected to ground and the other side provides a synchronization signal on line 90 to a synchronizer 92.

When the magnet 56 is OFF the photomultiplier 62 provides a normal atomic absorption signal on its output line 94 referenced to ground across resistor 96. This signal is supplied to a preamplifier 98. During the period when the magnet is OFF switch 100 is closed and the signal from the photomultiplier 62 which has been reduced by the sample absorbance and the background absorbance, passes through coupling capacitor 102 and is supplied to a linear integrator indicated schematically as capacitor 104 and amplifier 106. The signal from the integrator is supplied to a logarithmically scaled analog to digital converter 108. The digital signal is supplied to a microcomputer 110 and the microcomputer then supplies the information to a display generally indicated at 112. All of this is essentially the same as the situation when the same measurement is being made in the normal atomic absorption spectrophotometer 20 of FIG. 1.

When the magnet 56 is ON however, absorption by the element being measured occurs at one polarization at the central line and at the opposite polarization to either side of the central line. The polarization analyzer 50 is oriented so as to reject the central line polarization called $\pi$ and to accept the deviated line polarization called $\sigma$. In this way light from the line source 30' in the $\sigma$ polarization goes through the sample, is not absorbed by the sample when the magnet is ON, but passed through the polarization analyzer to the monochromator 60 and photomultiplier 62. Light of the $\pi$ polarization is deviated by the polarization analyzer and does not reach the monochromator 60. Since the spectral line from the line source 30 is narrower than the distance between the deviated $\sigma$ lines when the magnet is ON, the absorbance of the sample measured is essentially due to the non-atomic species of the sample and the signal on line 94 from the photomultiplier 62 is the background signal.

Synchronizer 92 is arranged to close switch 114 during this period. The signal is linearly integrated by capacitor 116 and amplifier 106 and supplied to log analog to digital converter 108 and then to the microcomputer 110. The subtraction of the field ON and field OFF system is made and the result displayed on display 112.

The integrated background signal is also supplied on line 118 to an automatic gain control circuit 120 which has a response time of about 100 milliseconds, for a 60 Hertz magnetic field frequency. The output of the automatic gain control circuit controls a high voltage power supply 122 supplying high voltage on line 124 to the photomultiplier 62. Thus the photomultiplier 62 is caused to produce the same output signal for any background absorbance, greatly increasing its range of sensitivity. We have discovered that the high voltage supplied on line 124 is in fact the log of the background signal, that is the background absorbance and therefore such a signal may be provided by a voltage divider 124 on line 128, digitalized by a linear analog to digital connector (not shown) and supplied to the microprocessor 110.

As is normal in synchronous detection the integrating capacitor 102 is referenced to ground before each measurement during the successive energizations of the magnet 56. This is accomplished by switch 130 which is energized when no light is being received by the photomultiplier tube 62. This is accomplished by turning lamp 130 off by means of a supply signal on line 132 from synchronizer 92.

Figures 4, 4A:
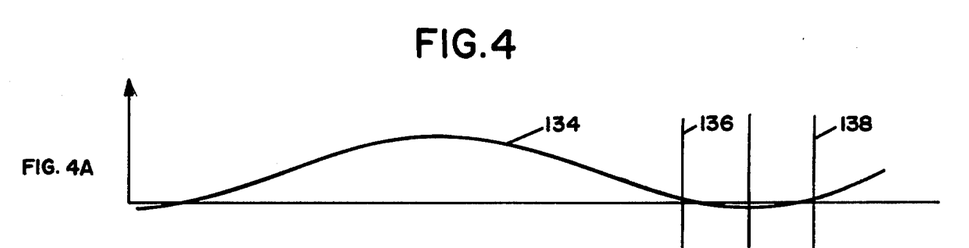
FIG. 4 is a timing diagram of the system of FIG. 3 and comprises FIGS. 4A through 4E, each showing a separate signal employed in the system.

The electrical operation of the Zeeman background correction instrument illustrated in FIG. 2 can be understood with reference to FIG. 4. FIG. 4A shows a plot of the magnetic field 134 which is essentially unipolar, except that it goes slightly negative between times 136 and 138 where the integral of the field between times 136 and 138 is substantially zero.

Figure 4B:
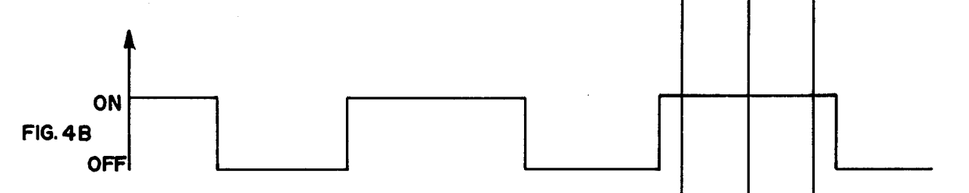

FIG. 4B shows a plot of the signal utilized to turn the lamp 30' on and off supplied on line 132. As can be seen, the lamp is turned on during maximum field and during minimum field periods.

Figure 4C:
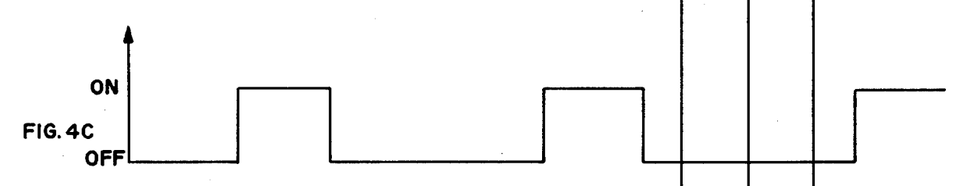

FIG. 4C is a plot of the operation of switch 130, the dark time clamp, which is on during a period while the line source 30' is off, as illustrated in FIG. 4B.

Figure 4D:
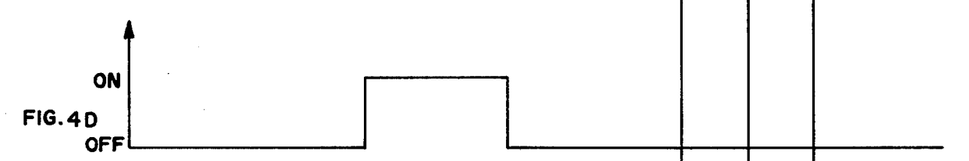

FIG. 4D is an illustration of the operation of the background or magnet ON switch 114 which is turned ON during the magnet ON period.

Figure 4E:
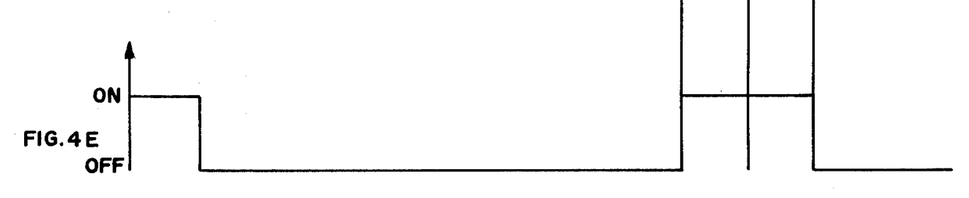

FIG. 4E is an illustration of the operation of the magnet OFF or sample plus background switch 100 which is closed during the magnet OFF period.

Those skilled in the art will understand that switches 100, 114 and 130 are idealy electronic switches controlled by the synchronizer 92 as indicated by the dotted lines.

Figure 5:
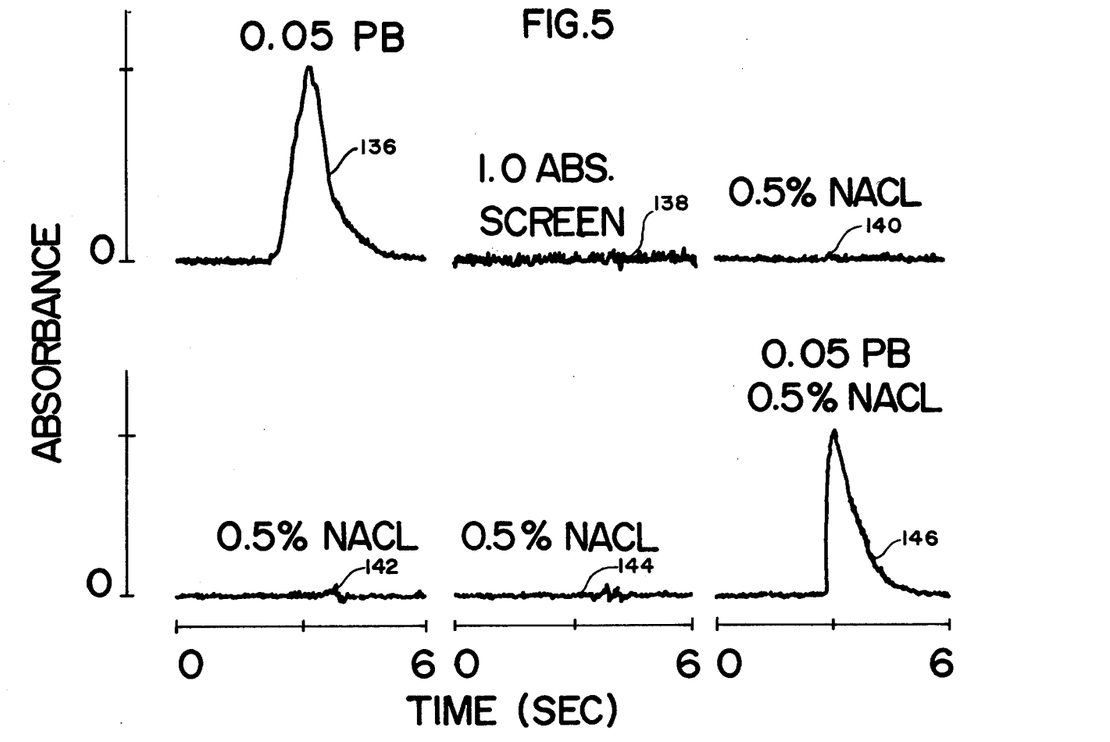
FIG. 5 is a series of plots of absorbance over time produced by the system of FIG. 3, illustrating the system's sensitivity in measuring the presence of 0.05 micrograms per milliliter of lead in a 0.5% sodium chloride solution.

FIG. 5 is a series of plots provided by the readout device 112 under control of the microprocessor 110 (FIG. 3). The microprocessor 110 is the same microprocessor provided in the Perkin-Elmer model 5000 and may operate with the same program. It is desirable however that rollover detection be provided when the output fed to the microcomputer 110 is from the Zeeman adapter 22, in order to prevent double valued readings.

Figure 6:
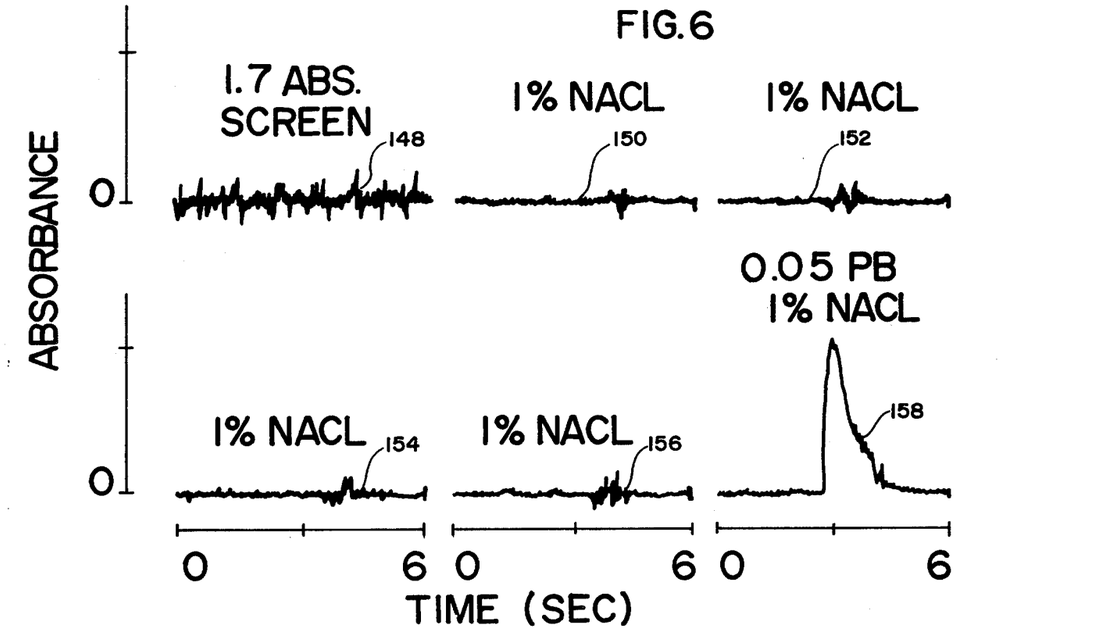
FIG. 6 is a series of plots similar to FIG. 5 illustrating the system's sensitivity in measuring the presence of 0.05 micrograms per milliliter of lead in a 1% sodium chloride solution.

FIG. 6 is a series of plots taken at the spectral line 283.3 nanometers utilizing a 10 microliter sample having a background absorbance of 1. The samples were supplied to the furnace 42 of the Zeeman adapter 22 of the invention. Curve 136 was produced when the sample contained 0.05 micrograms per milliliter of lead. Plot 138 is the result of a screen having an absorbance of one. Plot 140 is the result of incorporating 0.5% sodium chloride in the 10 microliter sample. Plots 142 and 144 are further runs with 0.5% sodium chloride. The final plot 146 is the result when 0.05 micrograms per milliliter of lead are incorporated in a 0.5% sodium chloride 10 microliter sample. It should be noted that the lead is as easily recognized as when there was no sodium chloride present, as illustrated in plot 136.

FIG. 6 is a series of runs also at 283.3 nanometers, of a 10 microliter sample with a background absorbance of 1.7. At this level nearly 99% of the light passing through the sample is absorbed by the background. Plot 148 is the result of a screen having an absorbance of 1.7. Plot 150 is of a run in which the sample included 1% sodium chloride, as are plots 152, 154 and 156. Plot 158 was generated when 0.05 micrograms per milliliter of lead were incorporated in the 1% sodium chloride solution. Again it should be noted how easy it is to measure the absorbance of the lead from plot 158, basically as easy as if there were no background, as in plot 136 of FIG. 5.

Figure 7:
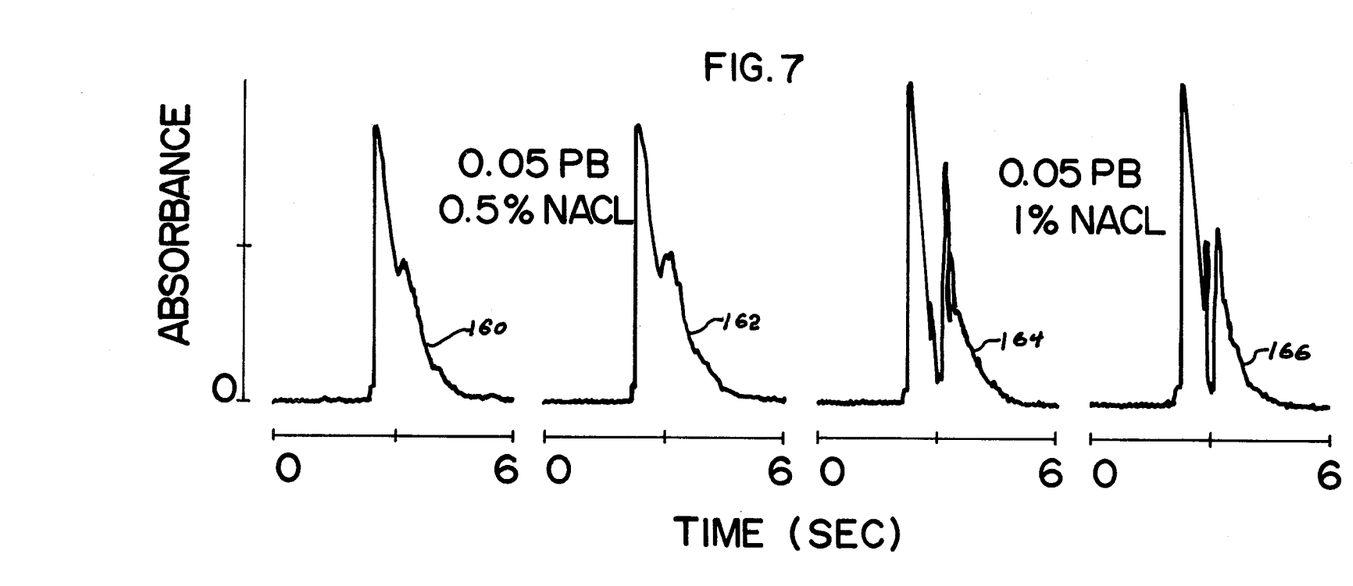
FIG. 7 is a series of plots produced by the prior art Perkin-Elmer Model 4000 spectrophotometer in measuring the presence of 0.05 micrograms per milliliter of lead in a 0.5% and in a 1% sodium chloride solution.

FIG. 7 is a series of plots also at 283.3 nanometers, a 10 microliter sample. However these plots were derived from supplying the sample to the Perkin-Elmer model 4000 atomic absorption spectrophotometer which is similar to the model 5000, utilizing conventional continuum source background correction. When 0.05 micrograms per milliliter of lead are incorporated in a 0.5% sodium chloride solution sample plots 160 and 162 were derived in separate 6 second runs. Note how much cleaner plot 146 of FIG. 5 is when the Zeeman adapter is utilized.

Plots 164 and 166 of FIG. 7 are two runs in the Perkin-Elmer 4000 where the sample included 0.05 micrograms per milliliter of lead in a 1% sodium chloride solution. Note that in plot 164 the lead absorbance is just barely greater than the background, whereas in plot 158 made on the Zeeman adapter, the background is still greatly suppressed.

Thus the Zeeman adapter of our invention is able to measure the absorbance of elements when the background absorbance is much greater than can be done in prior art instruments. We have achieved this in an instrument with a magnetic field strength of 8 kilogauss. Higher fields would increase separation of the $\pi$ and $\sigma$ lines and thus increase insensitivity to background absorbance.

Figure 8:
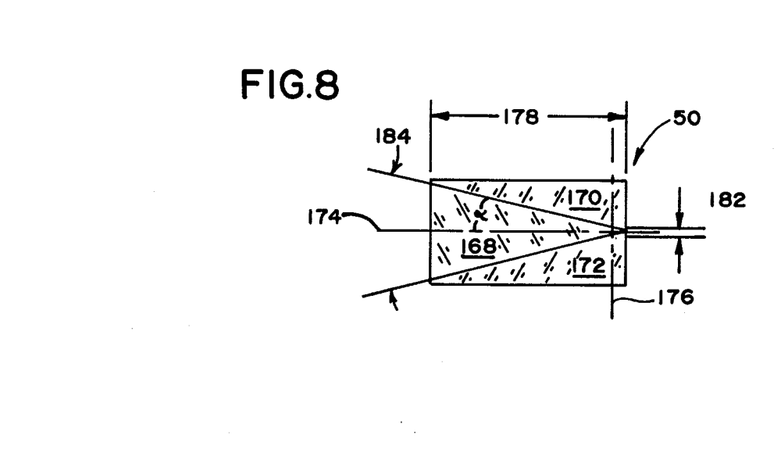
FIG. 8 is a top view of the polarization analyzer of FIG. 3 with the direction of light passage reversed from that shown in FIG. 3.
Figure 9:
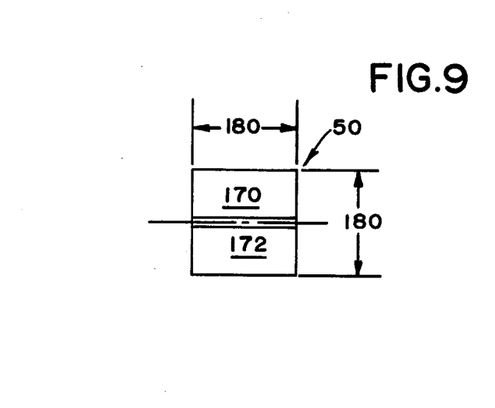
FIG. 9 is an end view of the exit face of the polarization analyzer of FIGS. 3 and 9.

The polarization analyzer 50 of the invention is illustrated in detail in FIGS. 8 and 9. It may be manufactured of any birefringent material usable at the spectral lines of interest. Because it is desirable to use the Zeeman adapter at the ultraviolet range from 190 nanometers to 850 nanometers, the material of the polarization analyzer 50 is preferably artificial crystal quartz or other transparent birefringent material suitable for use in this range, e.g. crystalline magnesium fluoride, or sapphire.

A quartz analyzer is illustrated in FIGS. 8 and 9 and comprises a wedge 168 having an isosceles triangle cross section, and a pair of right triangular cross section wedges 170, 172 in optical contact therewith. The principal optical axis of element 168 is shown at 174. The principal optical axis of elements 170 and 172 is at right angles thereto and is illustrated at 176. Optical axis 176 is aligned with the magnetic field of the electromagnet 56. The length 178 of the polarization analyzer 50 utilizing quartz having a principal optical index of refraction of 1.64927 and an extraordinary index of 1.6627 is 40 plus or minus 0.2 millimeters. As shown in FIG. 9 the analyzer 50 is square and the side dimensions 180—180 are 22 plus or minus 0.2 millimeters. Since the wedge 168 cannot come to a knifepoint, the flat on the apex thereof has a dimension 182 of about 0.50 millimeters.

As previously mentioned the analyzer 50 not only deviates the light from the furnace 42 which is polarized perpendicularly to the magnetic field, and passes the light which is parallel to the magnetic field, it also depolarizes the latter.

This depolarization occurs because light passing from wedges 170 and 172 into wedge 168 after passing the boundaries therebetween, is rotated in its plane of polarization by the birefringent wedge 168 in proportion to the distance it travels within it. This occurs because birefringent material acts as a circular rotator on polarized light traveling along its principal axis and the analyzer 50 is made long enough for several 360° rotations. Since various rays travel various distances, the exiting light includes all polarizations and is in effect depolarized, eliminating all polarization effects in the monochromator 60 and photomultiplier 62.

If other forms of polarization analyzers are used, for example, dichroic sheet at visable light frequencies, the same result of monochromator insensitivity may be produced by using a depolarizer after the analyzer.

Another advantage of the analyzer 50 is that the angle $\alpha$ in FIG. 8 is one half of that in a conventional Rochon analyzer. Since the deviation of the rejected rays is inversely proportional to $\alpha$, great deviation is achieved without lengthening the analyzer along the optic axis with its accompanying restriction of the field of view and increased use of expensive material.

This analyzer constructed out of three wedges has four times the light throughput of a Rochon analyzer constructed of two wedges of the same volume.

Those skilled in the art will understand that this depolarizing analyzer may be used in many other optical systems and in various spectrometers employing analyzers where it is desired to eliminate polarization effects at the monochromator.

It will thus be seen that the objects set forth above among those made apparent from the preceding description, are efficiently attained, and since certain changes may be made in the above described elements, constructions, and systems without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

Having described our invention what we claim as new and desire to secure by Letters Patent is:

1. In an atomic absorption spectrophotometer employing an electromagnetic optical effect for background correction and comprising an electromagnetic field producing device for producing the effect having a pair of input terminals; the improvement comprising: connecting the electromagnetic field producing device to a source of substantially single frequency alternating current; and a unidirectional conducting device connected in circuit with said electromagnetic field producing device to produce a substantially unidirectional field.

2. An atomic absorption spectrophotometer as defined in claim 1 said improvement further defined in that said electromagnetic field producing device is an electromagnet producing a magnetic field and said unidirectional conducting device is a solid state diode connected in series with said electromagnet and an alternating current power line.

3. The improvement defined in claim 2 and a capacitor connected across the input terminals of said electromagnet.

4. An atomic absorption spectrophotometer as defined in claim 1 and a time varying electromagnetic field producing device for producing a time varying electromagnetic optical effect, said field producing device having a pair of input terminals and a radiation responsive device producing an output signal which varies in time and at certain times is proportional to the background radiation and wherein said radiation responsive device is responsive to a linearly increasing supply signal to produce a exponentially increasing output signal upon receiving a fixed radiation level and means for controlling said supply signal; the further improvement comprising: connecting the electromagnetic field producing device to a source of substantially single frequency alternating current; and a unidirectional conducting device connected in circuit with said electromagnetic field producing device to produce a substantially unidirectional field; and means for supplying said background signal to said means for controlling said supply signal to said radiation responsive device whereby said supply signal is proportional to the log of the background absorption.

5. An atomic absorption spectrophotometer as defined in claim 1 and a polarization analyzer having a restricted angular field of view over which it properly operates as a polarization analyzer; time varying means for causing said electromagnetic optical effect for background correction and causing the spectrophotometer to provide time varying radiation; and a radiation responsive device producing an output signal which varies in time and at certain times is proportional to the background radiation; and wherein said radiation responsive device is responsive to a linearly increasing supply signal to produce an exponentially increasing output signal upon receiving a fixed radiation level and means for controlling said supply signal; the further improvement comprising: a field stop located between the analyzer and a source of radiation to be analyzed to restrict the radiation reaching said analyzer to an angle less than or equal to said restricted field of view; said polarization analyzer being formed of a single birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principal axes of said pair of wedges being perpendicular to said optical axis and to said apices; and means for supplying said background signal to said means for controlling said supply signal to said radiation responsive device whereby said supply signal is proportional to the log of the background absorption.

6. An atomic absorption spectrophotometer as defined in claim 4 and a polarization analyzer; the further improvement comprising: said polarization analyzer being formed of a single birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principal axes of said pair of wedges being perpendicular to said optical axis and to said apices.

7. An atomic absorption spectrophotometer as defined in claim 1 and a polarization analyzer; the further improvement comprising: said polarization analyzer being formed of a single birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principal axes of said pair of wedges being perpendicular to said optical axis and to said apices.

8. An atomic absorption spectrophotometer as defined in claims 1, and time varying means for causing said electromagnetic optical effect for background correction and causing the spectrophotometer to provide time varying radiation, comprising a radiation responsive device producing an output signal which varies in time and at certain times is proportional to the background radiation and wherein said radiation responsive device is responsive to a linearly increasing supply signal to produce an exponentially increasing output signal upon receiving a fixed radiation level and means for controlling said supply signal; the improvement comprising: means for supplying said background signal to said means for controlling said supply signal to said radiation responsive device whereby said supply signal is proportional to the log of the background absorption.

9. An atomic absorption spectrophotometer as defined in claim 1 and an electromagnetic field producing device having a pair of input terminals, a polarization analyzer having a restricted angular field of view over which it properly operates as a polarization analyzer; said electromagnetic field producing device is causing the spectrophotometer to provide time varying radiation, comprising a radiation responsive device producing an output signal which varies in time and at certain times is proportional to the background radiation and wherein said radiation responsive device is responsive to a linearly increasing supply signal to produce an exponentially increasing output signal upon receiving a fixed radiation level and means for controlling said supply signal; the improvement comprising: connecting the electromagnetic field producing device to a source of substantially single frequency alternating current; and a unidirectional conducting device connected in circuit with said electromagnetic field producing device to produce a substantially unidirectional field; a field stop located between the analyzer and a source of radiation to be analyzed to restrict the radiation reaching said analyzer to an angle less than or equal to said restricted field of view; said polarization analyzer being formed of a single birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principal axes of said pair of wedges being perpendicular to said optical axis and to said apices; and means for supplying said background signal to said means for controlling said supply signal to said radiation responsive device whereby said supply signal is proportional to the log of the background absorption.

10. In an atomic absorption spectrophotometer employing an electromagnetic optical effect for background correction and comprising a polarization analyzer having a restricted angular field of view over which it properly operates as a polarization analyzer; the improvement comprising: an electromagnetic field producing device for producing the electromagnetic optical effect having a pair of input terminals, said electromagnetic field producing device being connected to a source of single frequency alternating current; a unidirectional conducting device connected in circuit with said electromagnetic field producing device to produce a substantially unidirectional field, and a field stop located between the analyzer and a source of radiation to be analyzed to restrict the radiation reaching said analyzer to an angle less than or equal to said restricted field of view.

11. The atomic absorption spectrophotometer defined in claim 10 further comprising an atomic absorption furnace and a monochromator: said improvement further defined in that said field stop is located between said analyzer and said furnace and further limits the field of view of the monochromator such that the furnace's black body radiation is outside of said field of view of the monochromator.

12. An atomic absorption spectrophotometer as defined in claims 10 or 11, further comprising a diffraction grating: the further improvement of focusing means located between said grating and said polarization analyzer arranged to image said grating on the entrance face of the polarization analyzer such that the size of the image of the grating and the face of the polarization analyzer are substantially equal, whereby the face of the polarization analyzer acts as the aperture stop of the spectrophotometer.

13. The atomic absorption spectrophotometer defined in claims 10 or 11, further comprising a light source and optics between said light source and said field stop; said improvement further defined in that said field stop is imaged at said light source.

14. The atomic absorption spectrophotometer defined in claim 13, further comprising a diffraction grating: the further improvement of focusing means located between said grating and said polarization analyzer arranged to image said grating on the entrance face of the polarization analyzer such that the size of the image of the grating and the face of the polarization analyzer are substantially equal, whereby the face of the polarization analyzer acts as the aperture stop of the spectrophotometer.

15. In an atomic absorption spectrophotometer employing an electromagnetic optical effect for background correction and a polarization analyzer; the improvement comprising an electromagnetic field producing device for producing the electromagnetic optical effect having a pair of input terminals; said electromagnetic field producing device being connected to a source of single frequency alternating current; and a unidirectional conducting device connected in circuit with said electromagnetic field producing device to produce a substantially unidirectional field, and wherein said polarization analyzer being formed of birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principle axes of said pair of wedges being perpendicular to said optical axis and to said apices.

16. An atomic absorption spectrophotometer as defined in claim 15 wherein said improvement is further defined in that said birefringent material is chosen from the group consisting of quartz, magnesium fluoride and sapphire.

17. An atomic absorption spectrophotometer as defined in claims 15 or 16, wherein the adjacent faces of said wedges are in optical contact.

18. In an atomic absorption spectrophotometer employing time varying means for causing an electromagnetic optical effect for background correction and causing the spectrophotometer to provide time varying radiation, comprising: a radiation responsive device producing an output signal which varies in time and at certain times is proportional to the background absorption and wherein said radiation responsive device is responsive to a linearly increasing supply signal to produce an exponentially increasing output signal upon receiving a fixed radiation level and means for controlling said supply signal; the improvement comprising: means for supplying the background signal to said means for controlling said supply signal to said radiation responsive device whereby said supply signal is proportional to the log of the background absorption, and means utilizing said supply signal as a measure of the background absorbance.

19. An atomic absorption spectrophotometer as defined in claim 18 further defined in comprising means responsive to said time varying means for providing a time varying signal corresponding thereto, a synchronizer responsive to said time varying signal to provide three switching signals in synchronism therewith, and a first switch responsive to a first switching signal from said synchronizer to reference the output signal from said radiation responsive device to ground during periods when said output signal is substantially zero; a second switch for supplying said output signal to said supply signal controlling means, said second switch responsive to a second switching signal from said synchronizer to do such during periods when said electromagnetic optical effect is at a maxima and the radiation received from said radiation responsive device is the result of background absorption; analyzer means responsive to said background signal means; and a third switch for supplying said output signal to said analyzer means and responsive to a third switching signal produced by said synchronizer during the period when said electromagnetic optical effect is at its opposite maxima and the radiation received from said radiation responsive device is the result of sample and background absorption.

20. The atomic absorption spectrophotometer defined in claim 19 wherein said analyzer comprises integrator means to which said sample plus background signal and said background signals are provided alternately, an analog to digital converter to which the output of said integrator is provided, and a microcomputer to which the output signal to said analog to digital converter is supplied.

21. The atomic absorption spectrophotometer defined in claim 19 or 20, further comprising a source of atomic line radiation and an energization source therefore; said improvement further defined in that said synchronizer provides a fourth signal to said energization source to turn the source on only during periods when said electromagnetic optical effect is at its opposite maxima.

22. The atomic absorption spectrophotometer defined in claim 18, and an electromagnetic field producing device for producing the electromagnetic optical effect having a pair of input terminals; the further improvement comprising: connecting the electromagnetic field producing device to a source of single frequency alternating current; and a unidirectional conducting device connected in circuit with said electromagnetic field producing device to produce a substantially unidirectional field.

23. An atomic absorption spectrophotometer as defined in claims 1 or 18, and an electromagnetic field producing device for producing the effect having a pair of input terminals and a polarization analyzer having a restricted angular field of view over which it properly operates as polarization analyzer; the further improvement comprising: connecting the electromagnetic field producing device to a source of single frequency alternating current; and a unidirectional conducting device connected in circuit with said electromagnetic field producing device to produce a substantially unidirectional field; and, a field stop located between the analyzer and a source of radiation to be analyzed to restrict the radiation reaching said analyzer to an angle less than or equal to the effective field of view of the analyzer.

24. An atomic absorption spectrophotometer as defined in claims 1 or 18, and an electromagnetic field producing device for producing the electromagnetic optical effect having a pair of input terminals and a polarization analyzer having a restricted angular field of view over which it properly operates as a polarization analyzer; the further improvement comprising: connecting the electromagnetic field producing device to a source of single frequency alternating current; and a unidirectional conducting device connected in circuit with said electromagnetic field producing device to produce a substantially unidirectional field; a field stop located between the analyzer and a source of radiation to be analyzed to restrict the radiation reaching said analyzer to an angle less than or equal to said restricted field of view; and said polarization analyzer being formed of birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principle axes of said pair of wedges being perpendicular to said optical axis and to said apices.

25. An atomic absorption spectrophotometer as defined in claim 1 or 18, and a polarization analyzer having a restricted angular field of view over which it properly operates as a polarization analyzer; the further improvement comprising: a field stop located between the analyzer and a source of radiation to be analyzed to restrict the radiation reaching said analyzer to an angle less than or equal to said restricted field of view; and said polarization analyzer being formed of a single birefringent material and further comprising a first substantially wedge shaped piece of said material having its apex facing towards a source of radiation along an optical axis; the principal axis of said first wedge being along said optical axis and a pair of substantially wedge shaped pieces having their bases facing said source of radiation; one face of each of said pair of wedge shaped pieces being adjacent the opposite faces of said first wedge to form the polarization analyzer such that it has a substantially rectangular cross section perpendicular to the apices of the wedges; the principal axes of said pair of wedges being perpendicular to said optical axis and to said apices.

26. An atomic absorption spectrophotometer as defined in claims 1, 15 or 18, and a polarization analyzer having a restricted angular field of view over which it properly operates as a polarization analyzer; the further improvement comprising: a field stop located between the analyzer and a source of radiation to be analyzed to restrict the radiation reaching said analyzer to an angle less than or equal to said restricted field of view.

27. An atomic absorption spectrophotometer as defined in claims 1, 2, 10, 11, 15, 16, 18, 19, or 20 and an absorption cell and means for effecting said electromagnetic optical effect at said absorption cell.

28. An atomic absorption spectrophotometer as defined in claims 1, 15, or 18, and an absorption cell; means for analyzing the radiation from said absorption cell; and wherein all radiation directing means between the source of light illuminating said cell and said analyzing means are reflective elements each changing the direction of the optical axis between said absorption cell and said radiation analyzing device.

29. In an atomic absorption spectrophotometer employing an electromagnetic optical effect for background correction and comprising a polarization analyzer having a restricted angular field of view over which it properly operates as a polarization analyzer; the improvement comprising: a field stop located between the analyzer and a source of radiation to be analyzed to restrict the radiation reaching said analyzer to an angle less than or equal to said restricted field of view; and time varying means for causing said electromagnetic optical effect for background correction and causing the spectrophotometer to provide time varying radiation, including a radiation responsive device producing an output signal which varies in time and at certain times is proportional to the background radiation and wherein said radiation responsive device is responsive to a linerally increasing supply signal to produce an exponentially increasing output signal upon receiving a fixed radiation level, means for controlling said supply signal and means for supplying said background signal to said means for controlling said supply signal to said radiation responsive device whereby said supply signal is proportional to the log of the background absorption.

30. In an atomic absorption spectrophotometer employing an electromagnetic optical effect for background correction and comprising a polarization analyzer having a restricted angular field of view over which it properly operates as a polarization analyzer; comprising: a field stop located between said analyzer and a source of radiation to be analyzed to restrict the radiation reaching said analyzer to an angle less than or equal to said restricted field of view; and absorption cell; means for analyzing the radiation from said absorption cell; and wherein all radiation directing means between the source of light illuminating said cell and said analyzing means are reflective elements each changing the direction of the optical axis between said absorption cell and said radiation analyzing device.

31. An atomic absorption spectrophotometer as defined in claim 30 wherein said electromagnetic field producing device is an electromagnet.

* * * * *